(12) United States Patent
Maecke et al.

(10) Patent No.: US 7,192,570 B2
(45) Date of Patent: Mar. 20, 2007

(54) COMPOSITIONS OF SOMATOSTATIN ANALOGUES

(75) Inventors: Helmut Robert Maecke, Loerrach (DE); Jean Claude Reubi, Wabern (CH); Hans Rink, Bubendorf (CH); Klaus-Peter Eisenwiener, Bern (CH)

(73) Assignee: University of Bern, Bern (CH)

( * ) Notice: Subject to any disclaimer, the term of this patent is extended or adjusted under 35 U.S.C. 154(b) by 9 days.

(21) Appl. No.: 10/486,310

(22) PCT Filed: Aug. 7, 2002

(86) PCT No.: PCT/EP02/09004

§ 371 (c)(1),
(2), (4) Date: Jul. 21, 2004

(87) PCT Pub. No.: WO03/014158

PCT Pub. Date: Feb. 20, 2003

(65) Prior Publication Data
US 2004/0242842 A1     Dec. 2, 2004

(30) Foreign Application Priority Data
Aug. 10, 2002   (EP) ............................ 01203033

(51) Int. Cl.
*A61K 38/12* (2006.01)
*C07K 14/655* (2006.01)
(52) U.S. Cl. .................. 424/1.41; 514/11; 530/311
(58) Field of Classification Search ............ None
See application file for complete search history.

(56) References Cited

U.S. PATENT DOCUMENTS 4,261,885 A * 4/1981 Sakakibara et al. ......... 530/311
6,930,088 B2 * 8/2005 Hornik et al. ............... 514/9

OTHER PUBLICATIONS

International Search Report, Based on PCT/EP02/09004, Dated Nov. 29, 2002.

Scicinski, J. J., et al., "The solid phase synthesis of a series of tri-substituted hydantoin ligands for the somatostatin SST5 receptor," Bioorganic & Medicinal Chemistry Letters, Oxford, GB, vol. 8, No. 24, Dec. 15, 1998, pp. 3609-3614, XP004150376.

Reubi, J. C., et al., "A selective analog for the somatostatin SST1-receptor surtype expressed by human tumors," European Journal of Pharmacology, Amsterdam, NL, Mar. 12, 1998, pp. 103-110, XP000876543.

Hoyer, D., et al., "Classification and nomenclature of somatostatin receptors," Trends in Pharmacological Sciences, Elsevier Trends Journal, Cambridge, GB, vol. 16, No. 3, Mar. 1995, pp. 86-88, XP004207465.

* cited by examiner

*Primary Examiner*—Jeffrey Edwin Russel
(74) *Attorney, Agent, or Firm*—Patterson & Sheridan, L.L.P.

(57) ABSTRACT

In one embodiment, a composition of somatostatin analogues having the general formula:

Z-L-X1-X2-X3-X4-D-Trp-Lys-X5-X6 is provided wherein Z may be absent or present and when present is selected from DOTA- and DTPA-based chelators, NOTA-based chelators, carbonyl compounds, hydrazino nicotinamide, $N_4$-chelators, desferrioxamine, $N_xS_y$-chelators, optionally complexed or labeled with a radioisotope, tyrosine for halogenation, a fluorescent dye, or biotin. The composition further provides that L may or may not be present and when present is a linker molecule, X1 is glutamic acid or a symmetric or asymmetric diamino acid containing 3 or 4 consecutive C atoms, X2 is a positively charged natural or unnatural amino acid, an arginine mimic, citrulline, or a neutral amino acid, X3 is phenylalanine, Ala-[3-(2-thienyl)], α-naphthylalanine, or β-naphthylalanine, X4 is an aromatic amino acid, X5 is threonine or serine, and X6 is phenylalanine, Ala-[3-(2-thienyl)], α-naphthylalanine, or β-naphthylalanine.

34 Claims, No Drawings

COMPOSITIONS OF SOMATOSTATIN ANALOGUES

BACKGROUND OF THE INVENTION

1. Field of the Invention

The present invention relates to somatostatin analogues and their use in diagnosis and therapy. The invention also relates to pharmaceutical compositions comprising the novel analogues.

2. Description of the Related Art

Somatostatin (somatotroph release-inhibiting factor), was initially discovered as a hypothalamic neurohormone that inhibits growth hormone secretion. It is a widely distributed peptide in both the central and peripheral nervous system and is also present in peripheral tissues including the endocrine pancreas, gut, thyroid, adrenals and kidneys. In addition, somatostatin is produced by inflammatory and immune cells as well as many cancer cells.

In mammals, two forms of bioactive peptides, somatostatin 14 and somatostatin 28 are found. They are produced by tissue-specific proteolytic processing of a common precursor. The natural somatostatin peptides have a short half-life, which is why many somatostatin analogues have been synthesized. Among them, octreotide, lanreotide and vapreotide have been intensively investigated and are in clinical use for the medical treatment of acromegaly and neuroendocrine tumors. These octapeptides retain the amino acid residues (or substitutes) within a cyclic peptide backbone that are involved in the biological effect of the peptide ($Phe^7$ or $Tyr^7$, $D-Trp^8$, $Lys^9$ and $Thr^{10}$ or $Val^{10}$) and display markedly increased stability.

The biological effects of somatostatin are mediated by specific plasma membrane receptors that have been identified in normal and neoplastic tissues by binding studies and receptor autoradiography techniques. Five somatostatin receptor genes have been cloned from human and mammalian libraries and designated sst1 to sst5 receptors. The sst subtypes belong to the family of G protein-coupled receptors with seven transmembrane-spanning domains and present a high degree of sequence identity (39–57%). The sequence differences reside in the extracellular and intracellular domains and are probably responsible for their signalling specificity.

All somatostatin receptors bind somatostatin 14 and somatostatin 28 with a high affinity (nM range), although with a slightly higher affinity for somatostatin 14. However, the receptors show major differences in their affinities for peptide analogues. Analogues that are known to date exhibit a low affinity for sst1 and sst4 whereas they bind the sst2 and sst5 receptor with a high affinity, comparable to that of somatostatin 14 and bind the sst3 receptor with moderate affinity.

In addition to its effect on secretion and intestinal motility, somatostatin inhibits the proliferation of normal as well as tumor cells. The antiproliferative action of somatostatin can be signalled via the five sst receptors which initiate pertussis toxin-sensitive G protein-dependent cell growth arrest or apoptosis according-to receptor subtypes and target cells.

When expressed in CHO cells, ligand-activated sst1, sst2A, sst4, and sst5 receptors inhibit mitogenic signal of serum or growth factors as a result of hypophosphorylation of the retinoblastoma gene product (Rb) and $G_1$ cell cycle arrest.

However, distinct signal transduction pathways are involved in the somatostatin-induced $G_1$ cell cycle arrest depending on receptor subtype. The sst1 receptor mediates cell growth arrest through the stimulation of the tyrosine phosphatase SHP-2, activation of the Ras/MAP kinase ERK pathway and induction of the cyclin-dependent kinase inhibitor $p21^{waf1/Cip1}$, whereas the sst5 receptor acts by a mechanism involving a dephosphorylation cascade leading to inhibition of guanylate cyclase, cGMP-dependent protein kinase G and MAP kinase ERK 1/2.

The antiproliferative effect mediated by the sst2 receptor results from the activation of the tyrosine phosphatase SHP-1 and the dephosphorylation of activated growth factor receptors thus leading to the negative regulation of growth factor-induced mitogenic signalling.

In addition, somatostatin-activated SHP-1 induces a $G_1$ cell cycle arrest, upregulates the cyclin-dependent kinase inhibitor $p^{27Kip1}$ leading to the accumulation of hypophosphorylated Rb.

The antiproliferative effect of somatostatin can also result from apoptosis. Apoptosis is induced by sst3 as a result of the induction of p53 and Bax. In human pancreatic cancer cells expressing mutated p53 and devoid of endogenous sst2 receptor, correction of the deficit by expression of sst2 receptor induces an increase in cell death indicating that somatostatin can induce apoptosis by p53-dependent and p53-independent mechanisms.

The antiproliferative effects of somatostatin result from its actions via the endocrine pathway, but evidence exists that somatostatin can also act via an autocrine/paracrine pathway. Immunoreactive somatostatin has been found in somatostatin receptor-positive normal and tumor cell types such as endocrine, lymphoid cells, macrophages, breast cancer cells, colonic tumor cell and additionally, somatostatin mRNA is detected in a wide variety of neuroendocrine tumors known to express somatostatin receptors. Correction of the sst2 receptor deficit in human pancreatic cancer cells by sst2 receptor expression induces a negative autocrine loop in the absence of exogenous ligand, which is due to sst2 receptor-induced expression and secretion of endogenous sst2 ligand (somatostatin 14 and somatostatin 28). This results in inhibition of cancer cell proliferation and reversion of cell tumorigenicity in vitro and in vivo after xenografts in nude mice.

The somatostatin effect on tumor growth may be the result of indirect effects of the peptide resulting from the inhibition of secretion of growth-promoting hormones and growth factors which specifically regulate tumor growth. For example, the secretion of insulin-like growth factor-1 (IGF-1) which is produced by hepatocytes through GH-dependent and -independent mechanisms is negatively controlled by octreotide as a result of an effect on GH secretion and the sst2 and sst5 receptors have been demonstrated to be implicated in this effect. In addition, somatostatin can decrease IGF gene expression. Somatostatin also inhibits angiogenesis. Overexpression of peritumoral vascular somatostatin receptors with high affinity for somatostatin and octreotide has been reported in human peritumoral colorectal carcinomas, small cell lung carcinoma, breast cancer, renal cell carcinoma and malignant lymphoma. This expression appears to be independent of receptor expression in the tumor. It may reflect the presence of sst receptors in the venous smooth muscle cells as well as endothelial cells and may allow a vasoconstriction resulting in local hypoxia of the tumor or inhibition of endothelial cell growth and monocyte migration. Sst2, sst3 or sst5 receptors might be involved in these effects.

Although the biological role and cellular distribution of each receptor subtype are not yet completely understood it is clear that the development of analogues binding to all somatostatin receptor subtypes, so-called pansomatostatin, has high potential.

In one embodiment herein, it is thus an object of the present invention to provide such new somatostatin analogues that bind to all five somatostatin receptors and have a higher half-life (high metabolic stability) than somatostatin itself.

DETAILED DESCRIPTION

This is achieved according to the invention by somatostatin analogues of the general formula:

Z-L-X1-X2-X3-X4-D-Trp-Lys-X5-X6   (I)

wherein:
Z may be absent or present and when present is selected from the group consisting of DOTA- and DTPA-based chelators, NOTA-based chelators, carbonyl compounds, 2hydrazino nicotinamide (hynic), $N_4$-chelators, desferrioxamin, $N_xS_y$-chelators, all optionally complexed with a radioisotope, Tyrosine (Tyr) for halogenation, a fluorescent dye or biotin;
L may or may not be present and is a linker molecule;
X1 is a symmetric or asymmetric diamino acid, containing 3 or 4 consecutive C atoms with a linker to the chelating agent, for example D/L-diamino butyric acid (D/L-Dab) for a more basic character or D/L-Glu for coupling to primary and secondary amino groups;
X2 is a positively charged natural or unnatural amino acid or arginine mimic or citrulline, or a neutral amino-acid like Asn;
X3 is phenylalanine (Phe), Ala-[3-(2-thienyl)] or α-,β-naphthylalanine;
X4 is an aromatic amino acid, optionally halogenated, in particular with Cl, Br, I or $^{18}F$;
X5 is threonine (Thr) or serine (Ser); and
X6 is phenylalanine (Phe), Ala-[3-(2-thienyl)] or α-,β-naphthylalanine.

X1 is preferably diamino propionic acid or diamino butyric acid.

Preferably X2 is selected from the group consisting of Lysine (Lys), homolysine, I-Amp ornithine and

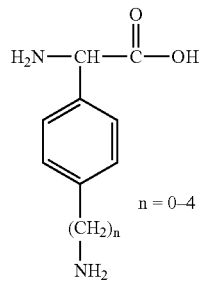

L/D-Phg(4-amidino) and derivatives.

When X2 is an arginine mimic it is preferably a group selected from:

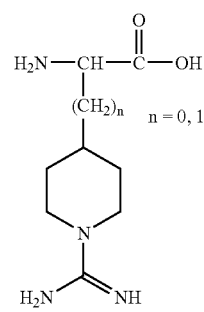

(R/S)-Gly/Ala-4-Pip(N-amidino)

D/L-Phe[4-guanidino] and derivatives thereof (R/S)-2-amino-4-[4-2-amino)-
pyrimidinyl]butanoic acid(n = 2)
and derivatives and quatemary ammonium derivatives ($NR_4^+$).

X4 is preferably selected from the group consisting of tyrosine (Tyr), halogenated tyrosine, in particular iodinated tyrosine (I-Tyr), dimethyltyrosine (diMe-Tyr), α-,β-Naphthylalanine, halogenated phenylalanine, in particular iodated phenylalanine (I-Phe). When X4 is halogenated this is preferably with Cl, Br or I.

When a linker L is present, it may be selected from the group consisting of tyrosine, lysine, diaminobutyric acid, diaminopropionic acid, polyethylene glycol, fatty acids and their derivatives, β-alanine, 5-amino valeric acid, sarcosine, gluceronic acid. Alternatively, the linker function may be taken on by X1. An example of a symmetric linker is

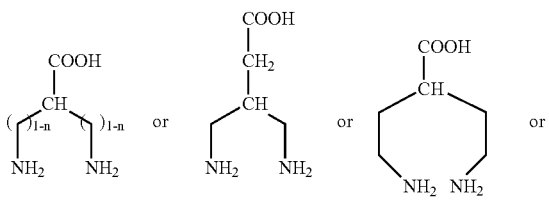

diamino acids, like diaminobutyric acid or 4,8 diaminooctanoic acid and symmetric molecules, like N,N-bis-(N'-3-aminopropyl)glycine.

In case Z is complexed with a radioisotope, the isotope may be selected from the group consisting of $^{67}$Ga, $^{68}$Ga, $^{103m}$Rh, $^{195m}$Pt, $^{114m}$In, $^{186}$Re, $^{188}$Re, $^{77}$As, $^{90}$Y, $^{66}$Ga, $^{67}$Cu, $^{169}$Er, $^{117m}$Sn, $^{121}$Sn, $^{127}$Te, $^{142}$Pr, $^{143}$Pr, $^{198}$Au, $^{199}$Au, $^{149}$Tb, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, $^{111}$Ag, $^{213}$Bi, $^{123}$I, $^{124}$I, $^{125}$I, $^{131}$I and $^{211}$At.

Preferred embodiments of the invention are somatostatin analogues of formula I wherein X2 is arginine, or wherein X3 is phenylalanine, or wherein X4 is phenylalanine, or wherein X4 is tyrosine, or wherein X5 is threonine, or wherein X6 is phenylalanine or wherein X1 is diaminobutyric acid.

The invention further relates to analogues wherein one or more of the above substituents are combined. In such analogues, the groups that do not have one of the above substituents are as defined for the general formula I above.

When all the above substituents are combined an analogue results having the general formula:

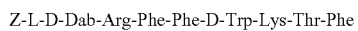

Z-L-D-Dab-Arg-Phe-Phe-D-Trp-Lys-Thr-Phe wherein Z may or may not be present and is as defined above. In preferred embodiments of the invention Z is DOTA, DOTAGA or tyrosine.

When X1 is D/L-Glu L are amine ending molecules like D/L-Lys, and Z are chelating agents like p-NH$_2$-Bz-DOTA (2-p-aminobenzyl-1,4,7,10-tetraazacyclododecane-1,4,7,10-tetraacetic acid), DOTA-p-NH$_2$-anilide (1,4,7,10-tetraazacyclododecane-1,4,7,10-tetraacetic acid mono(p-aminoanilide) and MeO—NH$_2$-Ph-DOTA (5-amino-2-methoxyphenyl-1,4,7,10-tetraazacyclododecane-1,4,7,10-tetraacetic acid).

Z may be complexed with a radioisotope, or coupled to a fluorescent dye or biotin. For use in diagnosis the analogue may be labeled with a radioactive metal isotope selected from the group consisting of $^{99m}$Tc, $^{203}$Pb, $^{67}$Ga, $^{68}$Ga, $^{72}$As, $^{111}$In, $^{113m}$In, $^{123}$I, $^{177}$Lu, $^{97}$Ru, $^{62}$Cu, $^{64}$Cu, $^{52}$Fe, $^{52m}$Mn, $^{51}$Cr, $^{124}$I and $^{18}$F.

Suitable fluorescent dyes are cyanin-dyews. Such dyes may be used when the analogues are applied in in vitro and in vivo diagnosis. Biotin is useful as a label in histology.

The somatostatin analogues of the invention can be used as a medicament in the treatment of diseases that are characterized by an overexpression of one or more somatostatin receptors, in particular the treatment may be directed to tumors bearing one or more somatostatin receptors. Examples of such tumours are neuroendocrinic tumors, astrocytoma, lung cancer, lymphoma, mama carcinoma, pancreatic tumors, thyroid cancer, colon cancer, SCLC, renal cell cancer.

For therapy, the somatostatin analogues of the invention may be labeled with a radioisotope selected from the group consisting of $^{114m}$In, $^{186}$Re, $^{188}$Re, $^{77}$As, $^{90}$Y, $^{66}$Ga, $^{67}$Cu, $^{169}$Er, $^{117m}$Sn, $^{121}$Sn, $^{127}$Te, $^{142}$Pr, $^{143}$Pr, $^{195m}$Pt, $^{198}$Au, $^{199}$Au, $^{149}$Tb, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, $^{103m}$Rh, $^{111}$Ag, $^{124}$I, $^{131}$I and $^{211}$At.

The invention also relates to the use of the somatostatin analogues for the preparation of a pharmaceutical composition for treatment or diagnosis.

In case the pharmaceutical composition is a diagnostic composition, the somatostatin analogue(s) is(are) labeled with a radioactive metal isotope selected from the group consisting of $^{99m}$Tc, $^{203}$Pb, $^{67}$Ga, $^{68}$Ga, $^{72}$As, $^{111}$In, $^{113m}$In, $^{123}$I, $^{177}$Lu, $^{97}$Ru, $^{62}$Cu, $^{64}$Cu, $^{52}$Fe, $^{52m}$Mn and $^{51}$Cr. When the pharmaceutical composition is a therapeutical composition, the somatostatin analogue(s) is(are) labeled with a radioisotope selected from the group consisting of $^{114m}$In, $^{186}$Re, $^{188}$Re, $^{77}$As, $^{90}$Y, $^{66}$Ga, $^{67}$Cu, $^{169}$Er, $^{117m}$Sn, $^{121}$Sn, $^{127}$Te, $^{142}$Pr, $^{143}$Pr, $^{198}$Au, $^{199}$Au, $^{149}$Tb, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, $^{103m}$Rh, $^{195m}$Pt, $^{111}$Ag, $^{124}$I, $^{131}$I and $^{211}$At.

The invention furthermore relates to a pharmaceutical composition comprising a suitable excipient and one or more of the somatostatin analogues.

The present invention will be further elucidated in the following examples that are given for illustration purposes only and are in no way intended to limit the invention.

EXAMPLES

Example 1

General Method for the Synthesis of Chelator-Somatostatin Analogues of the Invention The synthesis to the linear peptide intermediates is performed with well-established solid phase methods with Fmoc as transient amino portecting group, and TFA-labile side chain protection groups as Pbf for Arg, BOC for Trp and Lys, tBu for Thr. For a description of the method see "Fluorenylmehoxycarbonylpolyamide solid phase synthesis—A practical approach" by E. Atherton and R. C. Sheppard, Information Press Ltd., Oxford, England (1989). The Solid phase peptide synthesis is carried out on a semiautomatic peptide synthesiser.

The diaminobutyric acid is used with Fmoc as γ-amino protection group Z as α-amino protecting group. Coupling reactions are done with in-situ prepared hydroxy-benzotriazole esters with DIC, but any other coupling reagent may be used, e.g. the well introduced isourea derivatives (HATU etc.). The first amino acid (Fmoc-Phe-OH) is esterified to a super acid-labile linker (trialkoxy-benzhydryl or chlorotrityl) on the resin. After synthesis, the peptides are routinely cleaved mildly from the resin, using 20% acetic acid in dichloromethane. Coevaporation with toluene is performed two times leaving intact side-chain protection groups and therefore allowing subsequently cyclisation via carboxamide formation, using 10 equivalents of dicyclohexylcarbodiimide/hydroxybenzotrialoze in DMF at high dilution.

The crude product was extracted three times between ethyl acetate and a 5% aqueous oxalic solution and the organic layer was concentrated to dryness. The Z-protecting group is then selectively removed by catalytic hydrogenolysis, using Pd/C as catalyst in methanol, without significant affection of the indole system. The products were filtered and purified with a SepPak cartridge $C_{18}$ (Macherey-Nagel, Düren, Germany) using water and methanol as eluents. The resulting free amino acid group serves as an attaching point for a carboxylic functionalised chelator derivative, which may include an appropriate spacer. After the coupling to a prochelator, the peptide conjugate is deprotected with a solution of trifluoroacetic acid/phenole/thioanisol/water 85:5:5:5 for 2–5 hours. The final product was precipitated in isopropylether/petrolether 1:1 and purified by $C_{18}$ reverse phase chromatography (Metrohm LC CaDi 22-14, column: Macherey-Nagel, Düren, Germany) with a purity >98%.

Example 2

Synthesis of γ-9-fluorenylmetbyloxycarbonyl-α-benzyl-oxycarbonyl-D-diaminobuc acid (Z-Dab (Fmoc)-OH)

α-Benzyloxycarbonyl-D-diaminobutyric acid (Z-Dab-OH) is commercially available (Bachem, Bubendorf, Switzerland). This starting material was dissolved in acetone/water 1:1, sodium carbonate was added to a final pH of 9–10 and treated with 9-fluorenylmethyloxycarbonyl-N-hydroxysuccinimide (Fmoc-OSu). The reaction mixture was stirred for 18 hours at RT, cooled to 5° C.; ethylacetate was added and then acidified with 6 N HCl. The organic phase was washed with water four times, dried over sodium sulfate and concentrated. The product was recrystallised from ethylacetate/petrolether.

Example 3

Chelator Coupling

Three equivalents of prochelator (for example DOTAGA (tBU)$_4$ (1-(1-carboxy-3-carbotertbutoxypropyl)-4,7,10-(carbotertbutoxymethyl)-1,4,7,10-tetraazacyclododecane), DOTA(tBu)$_3$ (1,4,7-tris(carbotertbutoxymethyl)-10-carboxymethyl-1,4,7,10-tetraazacyclododecane), DTPA(tBu)$_4$ (1,1,7,7-tetrakis(carbotertbutoxymethyl)-4-carboxy-1,4,7-triazapentane) were incubated with 3 equivalents of HATU (O-(7-azabenzotriazol-1-yl)-N,N,N',N'-tetramethyluroniumhexafluorophosphate in DMF (dimethylformamide) for 30 min. The Z deprotected diamino acids (see above) were treated with this solution for 4 h at RT.

After concentration the mixture was dissolved in ethylacetate and extracted three times between 5% sodium hydrogencarbonate solution and ethylacetate. The organic layer was evaporated to dryness and the crude product is deprotected (see above).

A typical labeling procedure with $^{111}$In and $^{90}$Y is as follows. "PanSomatostatin" is one of the somatostatin analogues of the invention.

A buffer solution is prepared by dissolving 328 mg sodium acetate and 370 mg gentisic acid in 10 ml of water suprapure and adjusting the pH to pH 5 with 1 M sodium hydroxide.

10 μg of peptide (DOTA-PanSomatostatin), 100 μl of buffer and 120 μl of Yttrium-90 chloride (2.9 GBq/ml 0.05M HCl) were incubated at 95° C. for 40 min, cooled to room temperature and the labeling yield and radiochemical purity was determined by RP-HPLC using a Macherey-Nagel Nucleosil-$C_{18}$ column and a linear gradient from 5% acetonitrile/0.1% trifluoroacetic acid to 60% acetonitrile/0.1% trifluoroacetic acid in 30 min. The labeling yield is >98%.

10 μg of peptide (DOTA-PanSomatostatin), 100 μl of buffer and 100 μl of Indium-111 chloride (370 MBq/ml 0.05M HCl) were incubated at 95° C. for 40 min, cooled to room temperature and the labeling yield and radiochemical purity was determined by RP-HPLC using a Macherey-Nagel Nucleosil-$C_{18}$ column and a linear gradient from 5% acetonitrile/0.1% trifluoroacetic acid to 60% acetonitrile/0.1% trifluoroacetic acid in 30 min. The labeling yield is >98%. The stability is >87% after one week in 10000 times excess of DTPA and 76% in freshly prepared serum after one week, checked by HPLC. The serum proteins were precipitated with methanol, centrifuged and the methanol phase was injected, using the same gradient as above.

10 μg of peptide (DOTAGA-PanSomatostatin), 100 μl of buffer and 20 μof Yttrium-90 chloride (1.8 GBq/ml 0.05M HCl) were incubated at 95° C. for 40 min, cooled to room temperature and the labeling yield and radiochemical purity was determined by RP-HPLC using a Macherey-Nagel Nucleosil-$C_{18}$ column and a linear gradient from 5% acetonitrile/0.1% trifluoroacetic acid to 60% acetonitrile/0.1% trifluoroacetic acid in 30 min. The labeling yield is >98%. The radiochemical purity is >97% after 72 h. The stability is >87% after 72 h and >74% after one week in 10000 times excess of DTPA. Heating to 95° C. for 45 min did not impair the radiopeptide.

Example 4

Analysis of Affinity Profiles of Various Analogues for Somatostatin Receptors sst1–sst5

Cell culture CHO-K1 cells stably expressing human sst1 and sst5 were kindly provided by Drs. T. Reisine and G. Singh (University of Pennsylvania, Philadelphia, Pa.) and CCL39 cells stably expressing human sst2, sst3, and sst4 by Dr. D. Hoyer (Novartis Pharma, Basel, Switzerland).

CHO-K1 cells were grown in Ham's F-12 medium and CCL39 cells in Dulbecco's modified Eagle's medium/Ham's F-12 (1:1) mix, supplemented with 10% foetal bovine serum, 100 U/ml penicillin and 100 μg/ml streptomycin, in humidified air containing 5% $CO_2$ at 37° C. Geneticin (G418-sulfate; Gibco, USA) was used where necessary to maintain selection pressure at a final concentration of 400 μg/ml for sst2 to sst4—and 285 μg/ml for sst5—expressing cells as described previously [Rens-Domiano S & Reisine T. Biochemical and functional properties of somatostatin receptors. J. Neurochem. 58:1987–1996 (1992); OCaroll A et al., Characterization of cloned human somatostatin receptor SSTR5. Molec. Pharmacol. 46:291–298 (1994); Siehler S et al., [$^{125}$I]Tyr$^{10}$-cortistatin$_{14}$ labels all five somatostatin receptors. Naunyn-Schmiedeberg's Arch. Pharmacol. 357:483–489 (1998)].

All culture reagents were supplied by Gibco BRL, Life Technologies, Grand Island, N.Y.

Example 5

In situ Hybridisation Histochemistry

To control adequacy of the cell material, in situ hybridisation for human sst mRNAs was performed on CHO-K1 and CCL39 cells expressing the different sst receptor subtypes.

Cells were detached from culture flasks by washing with Puck's Saline A and brief incubation with trypsin (0.5 mg/ml)/EDTA (0.2 mg/ml), collected by centrifugation, and resuspended in phosphate-buffered saline at a final cell density of approximately $6 \times 10^4$ cells/µl. 25 µl Aliquots of cell suspension were spotted onto microscopic slides, air dried, and stored at $-20°$ C.

They were subsequently fixed with 4% formaldehyde, washed with phosphate-buffered saline, air dried, and stored at 4° C. under dry conditions. Cell smears were then used for sst1, sst2, sst3, sst4, and sst5 mRNA detection by in situ hybridisation. The protocol followed was essentially that described in detail previously [Reubi J C et al., Expression and localization of somatostatin receptor SSTR1, SSTR2 and SSTR3 mRNAs in primary human tumors using in situ hybridization. Cancer Res. 54:3455–3459 (1994)].

Oligonucleotide probes complementary to the sst1, sst2, sst3 [Reubi 1994, supra], sst4 and sst5 [Thoss VS et al., Expression of five somatostatin receptor mRNAs in the human brain and pituitary. Naunyn-Schmiedeberg's Arch. Pharmacol. 354:411–419 (1996)] mRNAs were synthesised and purified on a 20% polyacrylamide—8M urea sequencing gel (Microsynth, Balgach, Switzerland). They were labelled at the 3'-end by using $[\alpha^{32}P]$dATP (>3000 Ci/mmol; NEN Life Science Products, Boston, Mass.) and terminal deoxynucleotidyl-transferase (Boehringer, Mannheim, Germany) to specific activities of 33.3–74 GBq/mmol. Control experiments were carried out with the probes used in the present study to determine the specificity of the hybridisation signal obtained, as described previously [Reubi 1994, supra].

These control in situ hybridisation studies confirmed that the five cell lines used for the study expressed the correct sst mRNA.

Example 6

Receptor Autoradiograhy

Cells were washed twice with and scraped into ice-cold 0.05 M Tris-HCl (pH 7.4), collected by centrifugation, and homogenised using a rotor/stator slash system (Polytron, Kinematica Inc., Littau, Switzerland) in the same buffer. After centrifugation at 120 g for 5 min at 4° C., the supernatant was collected and centrifuged again at 48,000 g for 30 min at 4° C. The resulting pellet was resuspended in ice-cold Tris buffer, transferred into a microfuge tube, and centrifuged at 20,000 g for 15 min at 4° C. After withdrawal of the supernatant, the membrane pellet was stored at $-80°$ C.

Receptor autoradiography was performed on 20 µm thick cryostat (Leitz 1720, Rockleigh, N.J.) sections of the membrane pellets, mounted on microscope slides, and then stored at $-20°$ C. For each of the tested compounds, complete displacement experiments with the universal somatostatin radioligand $^{125}$I-[Leu$^8$, D-Trp$^{22}$, Tyr$^{25}$]-somatostatin 28 using increasing concentrations of the unlabelled peptide ranging from 0.1–1000 nM were performed. The unlabelled, universal somatostatin 28 was run in parallel using the same increasing concentrations, as control.

$IC_{50}$ values were calculated after quantification of the data using a computer-assisted image processing system as described previously [Reubi J C et al., Detection of somatostatin receptors in surgical and percutaneous needle biopsy samples of carcinoids and islet cell carcinomas. Cancer Res. 50: 5969–5977 (1990)]. Tissue standards (Autoradiographic [$^{125}$I] microscales, Amersham) that contain known amounts of isotope, cross-calibrated to tissue-equivalent ligand concentrations were used for quantification [Reubi J C. In vitro identification of vasoactive intestinal peptide receptors in human tumors: Implications for tumor imaging. J. Nucl. Med. 36: 1846–1853 (1995)]. Advantages of the present method using receptor autoradiography with sectioned cell pellets compared to binding on cell homogenates are, in addition to an economy on cells and a great flexibility, the greater inter-assay reliability and reproducibility, since the same embedded pellet can be used for successive experiments. As a minor disadvantage, $IC_{50}$ values are somewhat higher than in the homogenate binding assay.

The results are given in the following table. The compound tested is A:

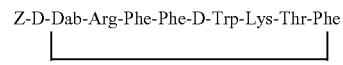

wherein Z is varied.

| | Z | hsst1 | hsst2 | hsst3 | hsst4 | hsst5 |
|---|---|---|---|---|---|---|
| ss28[1] | — | 2.9 | 1.8 | 4.6 | 3.0 | 2.3 |
| ss28 | — | 5.2 | 1.4 | 2.7 | 3.9 | 2.4 |
| ss28 | — | 5.2 | 2.8 | 3.8 | 5.7 | 3.8 |
| A | DOTA | 7.6 | 3.0 | 1.6 | 0.9 | 0.8 |
| A | Y-DOTA | 3.5 | 3.7 | 0.9 | 2.1 | 3.2 |
| A | Y-DOTA | 2.4 | 4.6 | 1.8 | 1.1 | 1.9 |
| A | Y-DOTA | 4.6 | 13 | 3.0 | 2.0 | 1.0 |
| A | Ga-DOTA | 6.0 | 5.2 | 3.0 | 4.1 | 1.0 |
| A | DOTAGA | 40 | 3.8 | 0.8 | 3.0 | 1.5 |
| A | DOTAGA | 24 | 3.8 | 2.5 | 2.3 | 1.9 |
| A | Y-DOTAGA | 64 | 7.5 | 1.0 | 8.0 | 3.1 |
| A | Y-DOTAGA | 34 | 5.0 | 2.6 | 4.4 | 2.7 |
| A | Tyr | 1.8 | 0.6 | 1.4 | 1.3 | 0.48 |
| A with X4 is Tyr | NH$_2$ | 24.5 | 2.9 | 2.0 | 1.0 | 0.8 |
| A with X4 is Tyr and X1 is GABA | — | 10.5 | 1.8 | 1.7 | 0.68 | 0.57 |
| minisomatostatin[2] | — | 172 | 2.8 | 3.2 | 15.3 | 6.8 |
| Arg-derivative[3] | | 20.0 | 4.0 | 2.5 | 10.6 | 2.7 |

Control substances:

[1] somatostatin 28

[2] ab-Asn-Phe-Phe-D-Trp-Lys-Thr-Phe

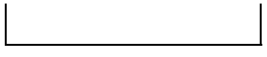

[3] ab-Arg-Phe-Phe-D-Trp-Lys-Thr-Phe

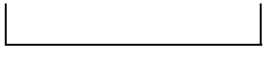

wherein ab is aminobutyric acid

The invention claimed is:

1. A composition of somatostatin analogues having the general formula:

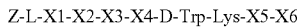

Z-L-X1-X2-X3-X4-D-Trp-Lys-X5-X6 wherein:
Z may be absent or present and when present is selected from the group consisting of DOTA-based chelators, DTPA-based chelators, NOTA-based chelators, carbonyl compounds, hydrazino nicotinamide, $N_4$-chelators, desferrioxamine, $N_xS_y$-chelators, tyrosine for halogenation, a fluorescent dye and biotin;
L may or may not be present and is a linker molecule;
X1 is a symmetric or asymmetric diamino acid containing 3 or 4 consecutive C atoms;
X2 is a positively charged natural or unnatural amino acid, an arginine mimic, citrulline, or a neutral amino acid;
X3 is phenylalanine, Ala-[3-(2-thienyl)], α-naphthylalanine, or β-naphthylalanine;
X4 is an aromatic amino acid;
X5 is threonine or serine; and
X6 is phenylalanine, Ala-[3-(2-thienyl)], α-naphthylalanine or β-naphthylalanine.

2. The composition of claim 1, wherein X2 is selected from the group consisting of diamino propionic acid and diamino butyric acid.

3. The composition of claim 1, wherein X2 is selected from the group consisting of lysine, I-Amp, ornithine, and L/D-Phg(4-amino).

4. The composition of claim 1, wherein X2 is the arginine mimic.

5. The composition of claim 1, wherein X4 is selected from the group consisting of tyrosine, halogenated tyrosine, iodinated tyrosine, dimethyltyrosine, α-naphthylalanine, β-naphthylalanine, and halogenated phenylalanine.

6. The composition of claim 1, wherein L is selected from the group consisting of tyrosine, lysine, β-alanine, sarcosine, succinic acid, and glutaric acid.

7. The composition of claim 1, wherein Z is complexed with a radioisotope selected from the group consisting of $^{114m}$In, $^{186}$Re, $^{188}$Re, $^{77}$As, $^{90}$Y, $^{66}$Ga, $^{67}$Cu, $^{169}$Er, $^{117m}$Sn, $^{121}$Sn, $^{127}$Te, $^{142}$Pr, $^{143}$Pr, $^{195m}$Pt, $^{198}$Au, $^{199}$Au, $^{149}$Tb, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, $^{111}$Ag, $^{123}$I, $^{124}$I, $^{125}$I, $^{131}$I, $^{203}$Bi, $^{211}$At, and $^{103m}$Rh.

8. The composition of claim 1, wherein X2 is arginine.

9. The composition of claim 1, wherein X3 is phenylalanine.

10. The composition of claim 1, wherein X4 is phenylalanine.

11. The composition of claim 1, wherein X4 is tyrosine.

12. The composition of claim 1, wherein X5 is threonine.

13. The composition of claim 1, wherein X6 is phenylalanine.

14. The composition of claim 1, wherein X1 is diamino butyric acid.

15. The composition of claim 1 having the general formula:

Z-L-D-Dab-Arg-Phe-Phe-D-Trp-Lys-Thr-Phe.

16. The composition of claim 1, wherein Z is DOTA.

17. The composition of claim 1, wherein Z is DOTAGA.

18. The composition of claim 1, wherein Z is tyrosine.

19. The composition of claim 1, wherein L is absent.

20. The composition of claim 1, further comprising a radioactive isotope selected from the group consisting of $^{99m}$Tc, $^{203}$Pb, $^{67}$Ga, $^{68}$Ga, $^{72}$As, $^{111}$In, $^{113}$In, $^{123}$I, $^{177}$Lu, $^{97}$Ru, $^{62}$Cu, $^{64}$Cu, $^{52}$Fe, $^{52m}$Mn, $^{51}$Cr, $^{124}$I and $^{18}$F.

21. The composition of claim 1, further contained within a pharmaceutical composition comprising a suitable excipient.

22. The composition of claim 21, further comprising a radioactive isotope selected from the group consisting of $^{99m}$Tc, $^{203}$Pb, $^{67}$Ga, $^{68}$Ga, $^{72}$As, $^{111}$In, $^{113m}$In, $^{123}$I, $^{124}$I, $^{18}$F, $^{177}$Lu, $^{97}$Ru, $^{62}$Cu, $^{64}$Cu, $^{52}$Fe, $^{52m}$Mn and $^{51}$Cr.

23. The composition of claim 21, further comprising a radioisotope selected from the group consisting of $^{114m}$In, $^{186}$Re, $^{188}$Re, $^{77}$As, $^{90}$Y, $^{66}$Ga, $^{67}$Cu, $^{169}$Er, $^{117m}$Sn, $^{121}$Sn, $^{127}$Te, $^{142}$Pr, $^{143}$Pr, $^{198}$Au, $^{199}$Au, $^{149}$Tb, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, $^{111}$Ag, $^{124}$I and $^{131}$I.

24. The composition of claim 1, wherein X1 is D/L-diamino butyric acid.

25. The composition of claim 1, wherein X1 is D/L-diamino propionic acid.

26. The composition of claim 1, wherein Z is a chelating agent selected from the group consisting of p-$NH_2$-Bz-DOTA, DOTA-p-$NH_2$-anilide, and MeO—$NH_2$-Ph-DOTA.

27. The composition of claim 1, wherein X2 is asparagine.

28. The composition of claim 1, wherein X4 is a halogenated aromatic amino acid.

29. The composition of claim 4, wherein the arginine mimic is selected from the group consisting of R/S-Gly-Ala-4-Pip(N-amidino), D/L-Phe(4-guanidino), and R/S-2-amino-4-[4-(2-amino)pyrimidinyl]butanoic acid.

30. The composition of claim 5, wherein X4 is iodated phenylalanine.

31. The composition of claim 1 having the general formula:

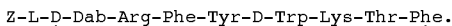

Z-L-D-Dab-Arg-Phe-Tyr-D-Trp-Lys-Thr-Phe.

32. A composition of somatostatin analogues having the general formula:

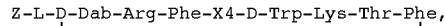

Z-L-D-Dab-Arg-Phe-X4-D-Trp-Lys-Thr-Phe, wherein:
Z may be absent or present and when present is selected from the group consisting of DOTA-based chelators, DTPA-based chelators, NOTA-based chelators, carbonyl compounds, hydrazino nicotinamide, $N_4$-chelators, desferrioxamine, $N_XS_Y$-chelators, tyrosine for halogenation, a fluorescent dye, and biotin;
L may or may not be present and is a linker molecule; and
X4 is Phe or Tyr.

33. The composition of claim 32, further comprising a radioactive isotope selected from the group consisting of $^{99m}$Tc, $^{203}$Pb, $^{67}$Ga, $^{68}$Ga, $^{72}$As, $^{111}$In, $^{113}$In, $^{123}$I, $^{124}$I, $^{18}$F, $^{177}$Lu, $^{97}$Ru, $^{62}$Cu, $^{64}$Cu, $^{52}$Fe, $^{52m}$Mn and $^{51}$Cr.

34. The composition of claim 32, further comprising a radioisotope selected from the group consisting of $^{114m}$In, $^{186}$Re, $^{188}$Re, $^{77}$As, $^{90}$Y, $^{66}$Ga, $^{67}$Cu, $^{169}$Er, $^{117m}$Sn, $^{121}$Sn, $^{127}$Te, $^{142}$Pr, $^{143}$Pr, $^{198}$Au, $^{199}$Au, $^{149}$Tb, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, $^{111}$Ag, $^{124}$I, and $^{131}$I.

* * * * *